United States Patent
Cannehan et al.

(10) Patent No.: US 9,333,330 B2
(45) Date of Patent: May 10, 2016

(54) MULTICHANNEL MICRO-NEEDLES

(75) Inventors: Francois Cannehan, Lausanne (CH); Astrid Cachemaille, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 0 days.

(21) Appl. No.: 13/384,569

(22) PCT Filed: May 19, 2010

(86) PCT No.: PCT/EP2010/056863
§ 371 (c)(1),
(2), (4) Date: Mar. 20, 2012

(87) PCT Pub. No.: WO2011/006699
PCT Pub. Date: Jan. 20, 2011

(65) Prior Publication Data
US 2012/0172820 A1    Jul. 5, 2012

(30) Foreign Application Priority Data

Jul. 15, 2009  (EP) ..................................... 09165602

(51) Int. Cl.
*A61M 37/00*    (2006.01)

(52) U.S. Cl.
CPC ..... *A61M 37/0015* (2013.01); *A61M 2037/003* (2013.01); *A61M 2037/0053* (2013.01)

(58) Field of Classification Search
CPC ................ A61M 37/0015; A61M 2037/0023; A61M 2037/003; A61M 2037/0038; A61M 2037/0053; A61M 2037/0061; A61K 9/0021
USPC ............................... 604/173, 21, 187, 22, 172
See application file for complete search history.

(56) References Cited

U.S. PATENT DOCUMENTS

| | | | |
|---|---|---|---|
| 2003/0015807 A1* | 1/2003 | Montemagno et al. | 257/798 |
| 2004/0164454 A1 | 8/2004 | Gartstein et al. | |
| 2004/0267205 A1* | 12/2004 | Stemme et al. | 604/173 |
| 2007/0255205 A1* | 11/2007 | Griss et al. | 604/93.01 |
| 2007/0275521 A1* | 11/2007 | Fu | 438/197 |
| 2007/0282281 A1* | 12/2007 | Ide et al. | 604/272 |
| 2008/0058726 A1* | 3/2008 | Jina et al. | 604/174 |
| 2009/0093776 A1* | 4/2009 | Yue et al. | 604/272 |
| 2009/0318833 A1* | 12/2009 | Lim | 600/573 |

(Continued)

FOREIGN PATENT DOCUMENTS

| | | |
|---|---|---|
| CN | 1830496 A | 9/2006 |
| CN | 1993156 A | 7/2007 |
| EP | 1669100 A1 * | 6/2006 |

(Continued)

OTHER PUBLICATIONS

International Search Report for PCT/EP2010/056863, mailed Aug. 16, 2010.
Written Opinion of the International Searching Authority for PCT/EP2010/056863, mailed Aug. 16, 2010.

(Continued)

*Primary Examiner* — Kami A Bosworth
(74) *Attorney, Agent, or Firm* — Nixon & Vanderhye P.C.

(57) ABSTRACT

A micro-needle (4) comprising a sharp tip (31), an elongated body (32) and a head (36) containing at least two parallel independent lumens (5, 6), each of said lumens (5, 6) communicating with a distal side opening (7, 8) of the head (36); said openings (7, 8) being essentially oriented in a direction which is perpendicular with respect to its lumen (5, 6) main direction and wherein the distal top end (33, 34) of said lumen (5, 6) is in the head (36) of the micro-needle (4).

14 Claims, 9 Drawing Sheets

(56) References Cited

U.S. PATENT DOCUMENTS

2010/0006536 A1* 1/2010 Kalvesten et al. ............. 216/11
2010/0256594 A1* 10/2010 Kimmell et al. ............. 604/506

FOREIGN PATENT DOCUMENTS

| JP | 2002-239014 | 8/2002 |
| JP | 2007-532245 A | 11/2007 |
| WO | WO 02/17985 A2 | 3/2002 |
| WO | WO 03/015860 | 2/2003 |

OTHER PUBLICATIONS

Chinese Office Action dated Apr. 8, 2013 and its English translation for applicant's Chinese Patent Application No. 201080031706.4 that corresponds to Applicant's PCT/EP2010/056863 filed May 19, 2010.
McAllister, D.V., et al, PNAS / Nov. 25, 2003, vol. 100, No. 24, pp. 13755-13760, "Microfabricated needles for transdermal delivery of macromolecules and nanoparticles: Fabrication methods and transport studies."
Japanese Office Action mailed Feb. 25, 2014, and its English translation for Japanese Patent Application No. 2012-519945 that corresponds to Applicant's PCT/EP2010/056863, filed on May 19, 2010.

* cited by examiner

← 101

← 101

← 101

← 101

MULTICHANNEL MICRO-NEEDLES

This application is the U.S. national phase of International Application No. PCT/EP2010/056863, filed 19 May 2010, which designated the U.S. and claims priority to Europe Application No. 09165602.5, filed 15 Jul. 2009, the entire contents of each of which are hereby incorporated by reference.

TECHNICAL FIELD

The present invention relates to micro-needles that can be used for the delivery of drugs, for example for a transdermal and/or intradermal fluidic delivery of such drugs.

BACKGROUND ART

In biomedical applications, it has become important to deliver small quantities of liquids through the stratum corneum of humans into the underlying tissue or also to sample fluids from the underlying tissue. For this purpose, micro-needles have been developed. Due to their small dimensions they can be inserted into the skin without pain and cause less tissue damage than conventional hypodermic needles. In the field of transdermal and/or intradermal application the micro-needles have the potential to become the preferred drug delivery device.

Micro-needles are usually split in two main categories: solid or hollow micro-needles. Solid micro-needles do not in principle allow an active administration of a substance such as a drug but rather use a coating of the needle to deliver the substance through the skin.

In the case of hollow needles, they have a channel or lumen that is able to direct the substance through the skin. Different hollow out-of-plane micro needle for transdermal and/or intradermal applications have been described in the past. They are usually arranged in two dimensional arrays to decrease flow resistance through the device. The array can be achieved with wafer level processing. The openings are at the top of the needle, a design that increases the risk of clogging or coring. Examples of such needles are disclosed for example in the following patents: U.S. Pat. No. 6,132,755 and U.S. Pat. No. 6,334,856, the content of which is incorporated by reference in its entirety in the present application.

Other different designs exist for example with a traversing hole opening at the tip of the needle (see for example D. V. McAllister et al. <<Microfabricated needles for transdermal delivery of macromolecules and nanoparticles: fabrication methods and transport studies>>, Proc. Natl. Acad. Sci. U.S.A, vol. 100, no. 24, pp. 13755-60, 2003) or to a side as disclosed in WO 02/17985 or in US 2004/0267205 and in WO 03/015860, all entirely incorporated by reference in the present application More specifically, patent publications US 2004/0267205 and WO 03/015860, corresponding to EP 1 416 996 (all entirely incorporated by reference in the present application) disclose micro-needles and a method for manufacturing said micro-needles. According to these publications, the micro-needle usually protrudes from a support member and comprises a micro-needle body portion, a closed pointed tip portion closing off a lumen in the tip region, and a cylindrical inner lumen extending through said support member and into said protruding needle. The needle body portion has at least one side opening communicating with said inner lumen, and the exterior envelope surface of the needle structure intersects the envelope surface of the cylindrical inner lumen within the needle structure in at least one defined region, so as to create at least one side opening in said body.

Such micro-needles and other known ones have one single inner lumen for the drug passage and one or several openings for the drug administration itself. Even if they have several openings, they still have one single supplying lumen. In case of obstruction for example by a particle or a part of the skin, a common risk considering the sizes of these needles, the needle becomes then useless. The single hole also has either a small diameter, thus a high flow resistance, or a large diameter making the needle more fragile.

Micro-blades with several lumens are disclosed in US 2009/0093776 A1. They however don't show a tip at their distal end but a blade. The related openings are furthermore not designed (and may not be used) for a tip.

Micro-needles with several lumens are disclosed in US 2004/0164454 A1. Their openings are however oriented in a way that the risk of obstruction is very high.

SUMMARY OF THE INVENTION

It is therefore an aim of the present invention to improve the known micro-needles and to overcome the drawbacks of known devices and methods.

More specifically, an aim of the present invention is to provide improved micro-needles of the type disclosed in US 2004/0164454.

Another aim of the present invention is to provide micro-needles that have a better shape and a better functioning. These micro-needles allow a better penetration into the skin due to an extremely sharp tip <1 µm.

Another aim of the present invention is to provide micro-needles that have a multiple channels or lumens (both words being used indifferently in the following description) offering an overall smaller flow resistance, while being more resistant to breakage and present less risk of being blocked by particles or skin parts. At least one of these side-openings is essentially perpendicular to the lumen axis.

More precisely the invention relates to a micro-needle comprising a conical sharp tip and an elongated body containing at least two parallel independent lumens, each of said lumens communicating with a distal side opening of the elongated body; said openings being essentially oriented in a direction which is perpendicular with respect to its lumen main direction and wherein the distal top end of said lumen is at least partially closed by said tip.

An essential feature of the invention is to form several lumens in the needle instead of a single lumen thus diminishing the risk of obstruction. In addition, if one lumen is closed or blocked, there is still at least another lumen that can be used for the delivery of drug or other products.

Another advantage of the present invention is to be able to deliver different drugs with the same device during the same injection or sequentially through the different channels.

A further advantage is that the same micro-needle can be used for the delivery of drug in one channel (or several channels) and simultaneously for the removal of another liquid by another channel (or by several channels). An example of use being the sampling of interstitial fluid for glucose measuring, while administering insulin in another channel. Another example of use in the field of diagnostics is the sampling of interstitial fluid in several independent channels with a separate measurement in each one of the channels and comparison of the value measured or sequential measurement in each channel at different time intervals.

A further advantage is the opportunity to create variable size of channels, depending on the flow resistance needed. In the event of variable delivery rates needed for different drugs, a same fluid pressure would result in variable delivery rates depending on each channel used. The same would apply in the event where fluid delivery and sampling would require different flow resistance according to the injection site. An example would be that a large channel would be used for the sampling, given the low interstitial fluid pressure, and a small channel for the drug delivery given a controlled higher pressure or required lower flow rate for the drug to be delivered.

As mentioned, depending on the number of channels in the needle, each channel or combination of channels may have a dedicated use (injection and/or removal).

DETAILED DESCRIPTION

The invention will be better understood from the following description of embodiments thereof and of the accompanying figures.

Figure 1:
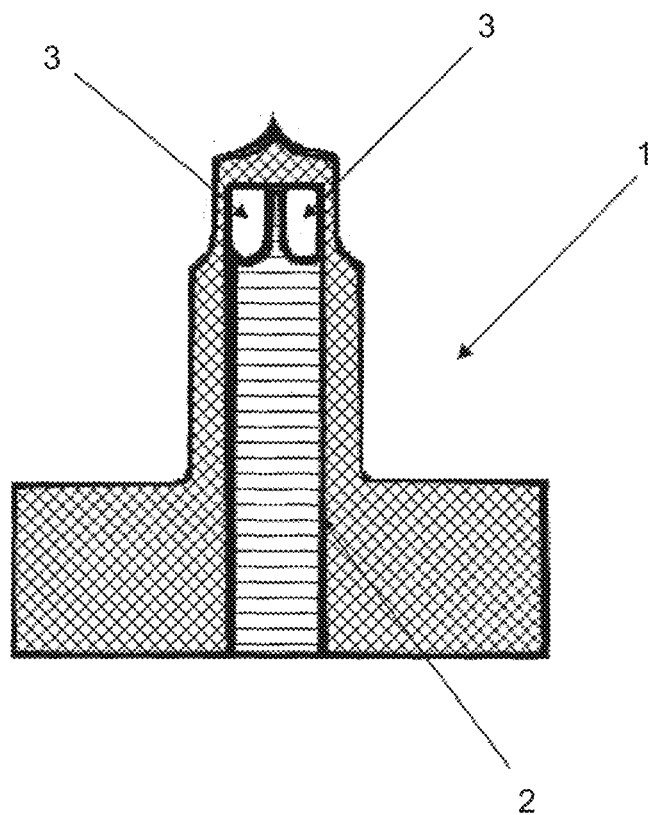
FIG. 1 illustrates an example of a needle of the prior art according to US 2004/0267205 or WO 03/015860.

In FIG. 1, as mentioned above, an example of a micro-needle 1 according to the prior art (such as in US 2004/0267205) is illustrated. This micro-needle comprises one single delivery channel 2 and several side openings 3 for the delivery of drug. For further description of this prior art design, reference is made to the cited patent publications that are incorporated by reference in the present application for this purpose.

In the following, we present and discuss the wafer level fabrication process for the out-of-plane silicon multi-channels micro-needles (See FIG. 2).

The fabrication of side-opened micro-needle is a double side process (frontside and backside) and is based on etching process. We used a combination of Deep Reactive Ion Etching (DRIE) which is a dry etching and wet etching in order to obtain the desired shape for the micro-needles.

Figure 2A:
FIG. 2 shows in cut view the process flow of the present invention.
Figure 2B:
Figure 2C:
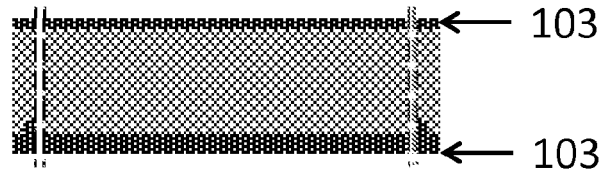
Figure 2D:
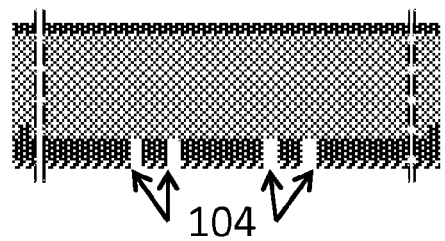
Figure 2E:
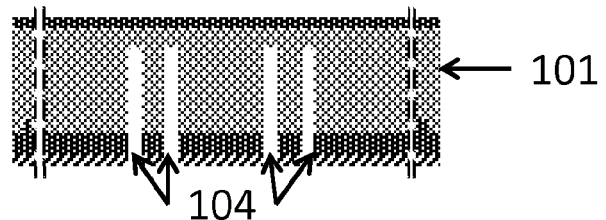
Figure 2F:
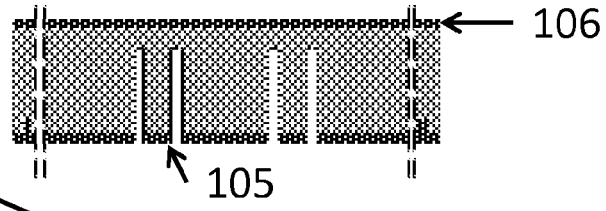
Figure 2G:
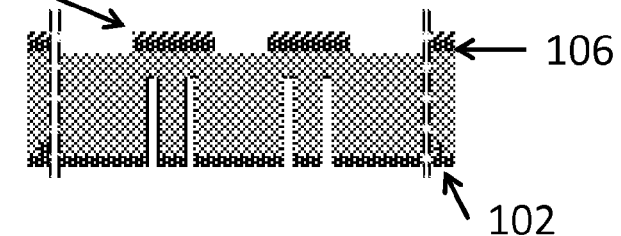
Figure 2H:
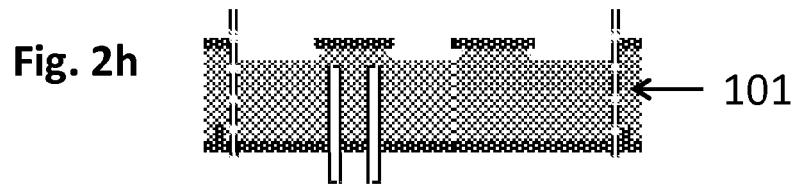
Figure 2I:
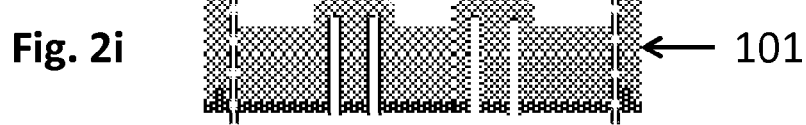
Figure 2J:
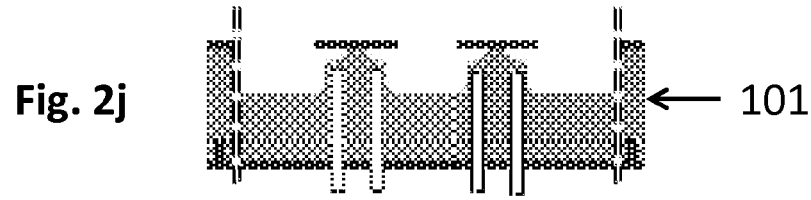
Figure 2K:
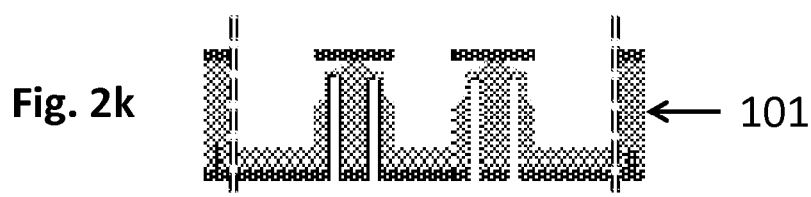

We start with a silicon wafer which has a sufficient thickness to obtain desired micro-needles height. A first photolithography is realized to pattern reference alignment marks into silicon wafer (FIG. 2a). This first step can be realized on the frontside or on the backside. It allows an excellent alignment between the frontside mask(s) and the backside mask(s) since each mask is aligned to these reference marks. A hard mask ($SiO_2$ or other suitable material) is deposited on the backside and on the frontside (FIG. 2c). This hard mask has to be thick enough to guarantee the backside silicon deep etching. A second photolithography is used to pattern the channels shape hole into this hard mask (FIG. 2d). A deep dry etching is realized into the backside of the wafer (FIG. 2e). This deep dry etching is obtained in a plasma etcher (ICP, RIE or other suitable equipment) and is obtained by cryogenic process or Bosch process. A protective layer is then deposit on the backside ($SiO_2$ by wet oxidation or other suitable material and method) to protect the backside holes (FIG. 2f). A hard mask ($SiO_2$ or other suitable material) is deposited on the frontside and is thick enough to guarantee the frontside silicon deep etching. A new photolithography is used to pattern a round shape into this hard mask (FIG. 2g). This round shape is perfectly aligned to the backside cylindrical shape thanks to the reference marks. The diameter of the hole must necessarily be smaller than the diameter of the frontside round shape. The patterning of the micro-needle is obtained by a succession of isotropic etchings and anisotropic etchings (FIG. 2h-l).

Figure 2L:
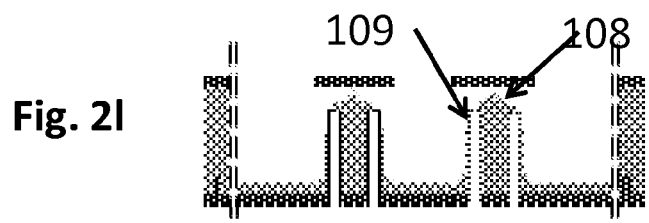
Figure 2M:
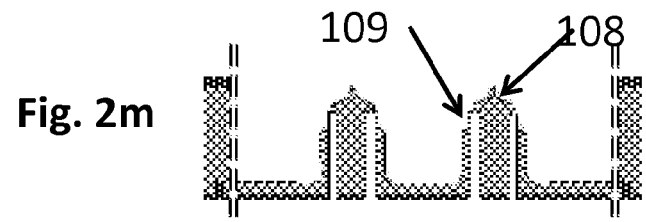
Figure 2N:
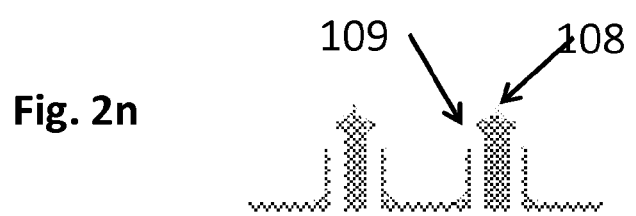

We need at least three isotropic etchings and 2 anisotropic etchings to obtain such micro-needle. In all configurations, the last step is an isotropic etching (FIG. 2l). We stop the process just when the mask falls off in order to guarantee an extremely sharp tip for the microneedle. The thickness of the mask is calculated in order to etch this entire mask at the end of the fabrication of the microneedle. A final wet oxidation (FIG. 2m) followed by a SiO2 strip (HF strip) is realized (FIG. 2n). This last step improves once again the tip of the microneedle and improves the roughness of the microneedle. The side openings appear during this last isotropic etching but it also possible they appear during a previous isotropic etching.

This process describes the wafer level fabrication process for the out-of-plane silicon multi-channels micro-needles but this fabrication process is also applicable for different out-of-plane side-opened silicon micro-needle configurations and/or dimensions. This fabrication process is applicable for example if we have one or more micro-needle, if we have one or more channels per micro-needle, for different micro-needle lengths or lateral dimensions.

Figure 3:
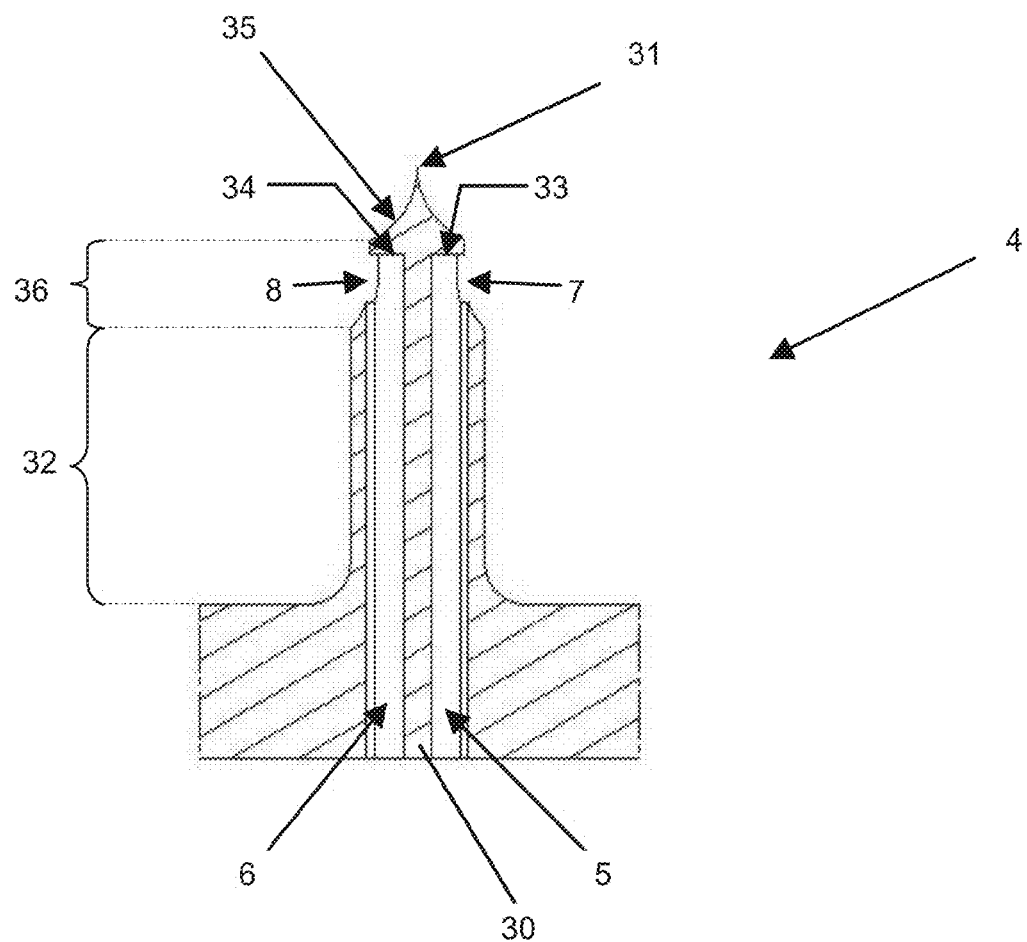
FIG. 3 illustrates in cut view an embodiment of the present invention.

FIG. 3 illustrates in axial cut view an embodiment of a micro-needle 4 according to the principle of the present invention. The micro-needle 4 contains at least two independent lumens 5, 6 each ending at the head 36 of the needle 4 in an opening 7 and 8. The distal top end 33, 34 of the lumen 5, 6 is in the head 36 of the microneedle 4.

In the present text, "tip 31" or "sharp tip 31" has to be understood as a conical part located at the distal end 35 of the micro-needle 4 and the "elongated body 32" and the head 36 are vertical elements, preferably cylinders, which are located between the tip 31 and the base 17.

Figures 4A, 4B:
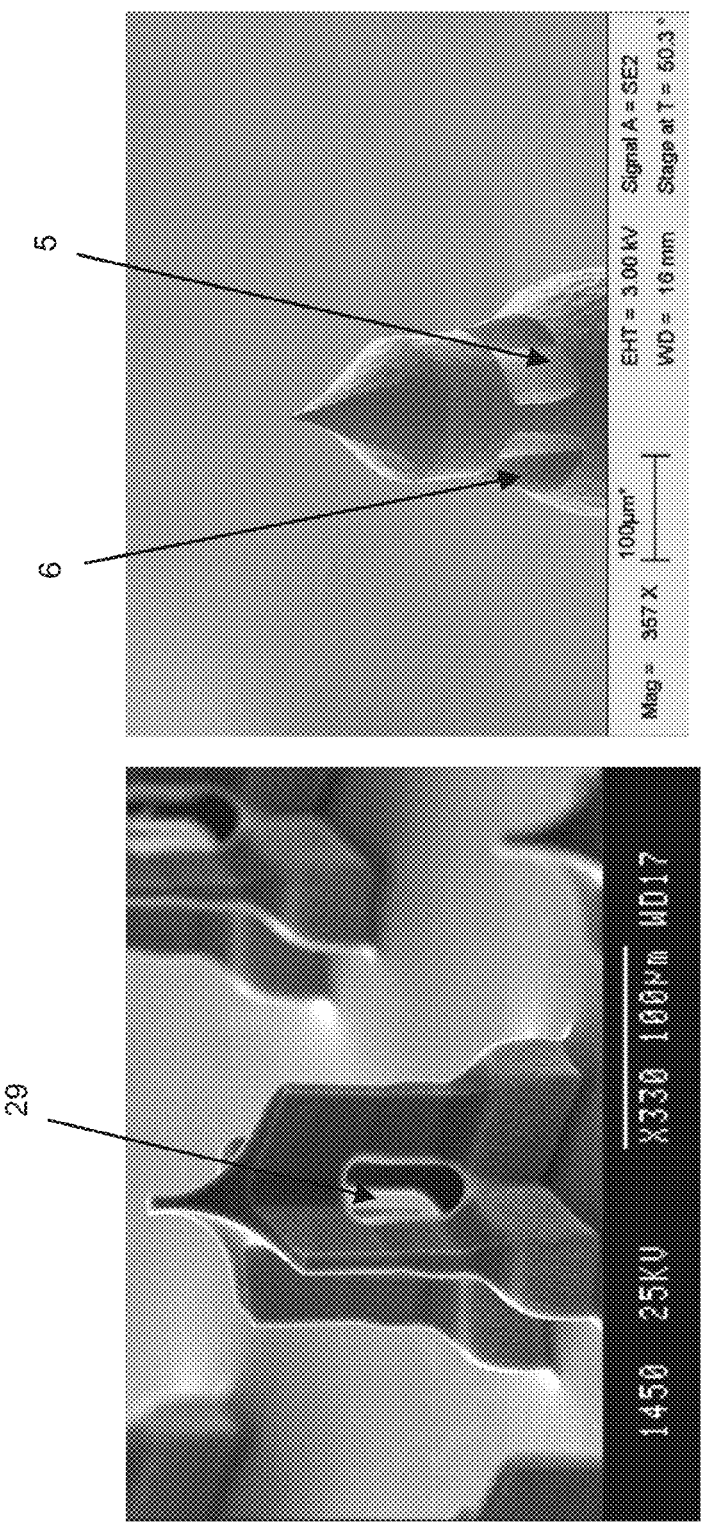
FIG. 4 illustrates a comparison between the tip of the prior art according to US 2004/0267205 or WO 03/015860 and the tip of the present invention

In FIG. 4, as mentioned above, a comparison between the tip of a micro-needle according to the prior art (FIG. 4a with only one channel 29 and four side-openings), such as in US 2004/0267205, and the tip of the present invention (FIG. 4b with independent channels 5, 6) is illustrated.

Figure 5:
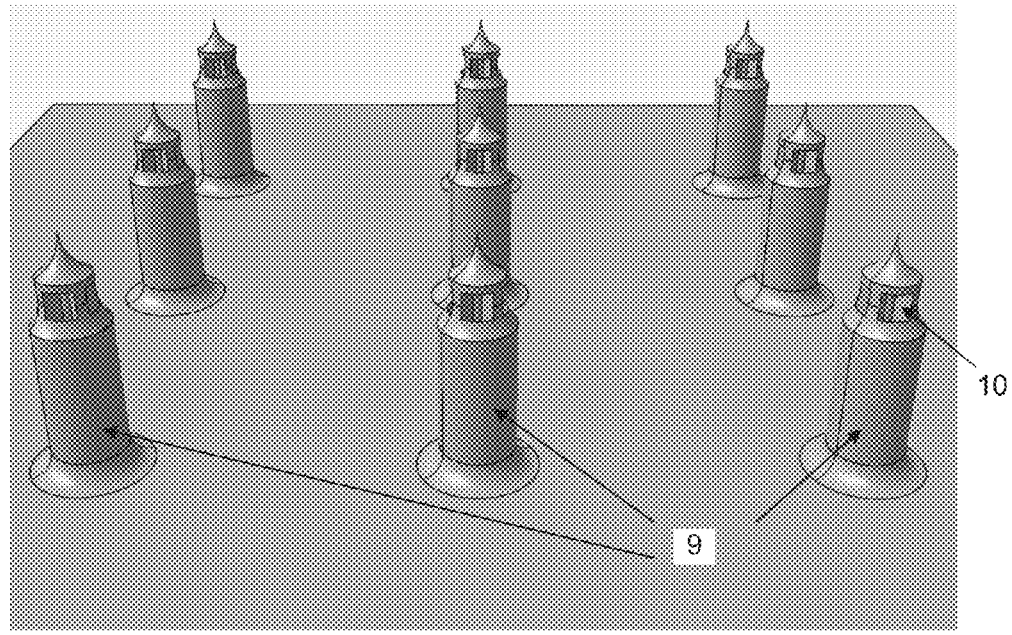
FIGS. 5 and 6 illustrate perspective views of a set of needles according to the invention.
Figure 6:
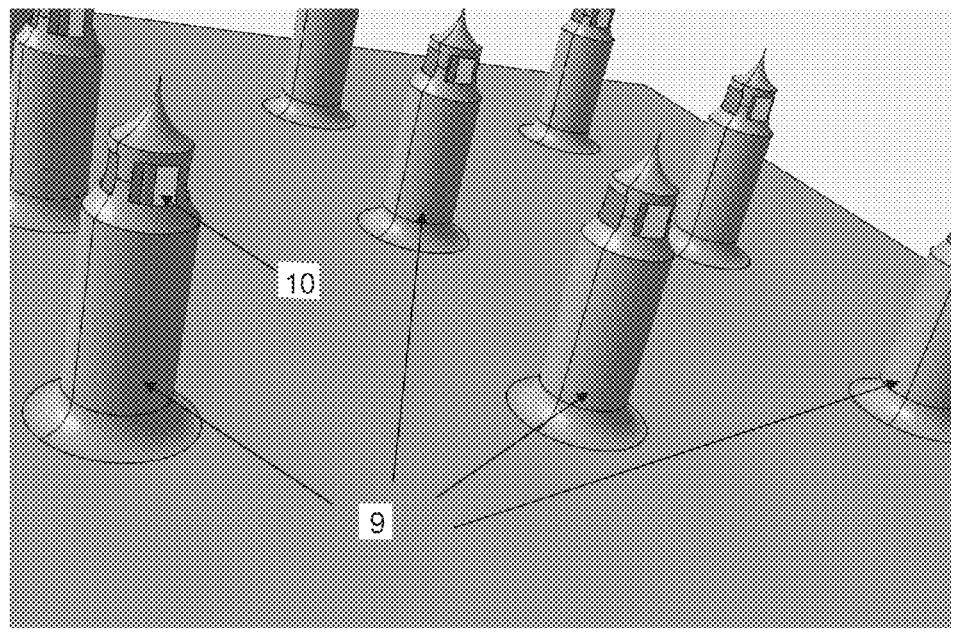

FIGS. 5 and 6 illustrate perspective views of a set of nine micro-needles 9 made according to the principle of the present invention. These micro-needles have each four channels, according to the principle of the present invention ending in four corresponding openings 10 near the tip of the needle.

Figure 7:
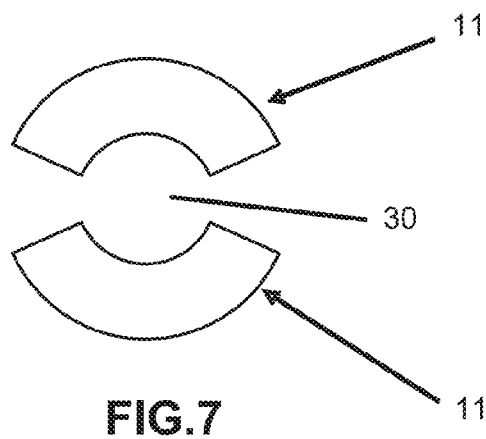
FIGS. 7 to 9 illustrate different configurations of multi-channels micro-needles in cut view.
Figure 8:
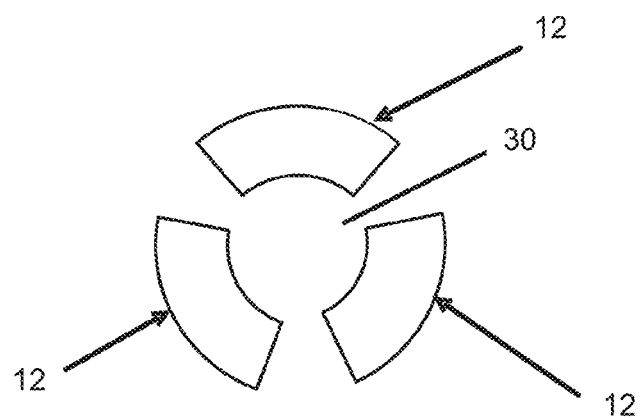
Figure 9:
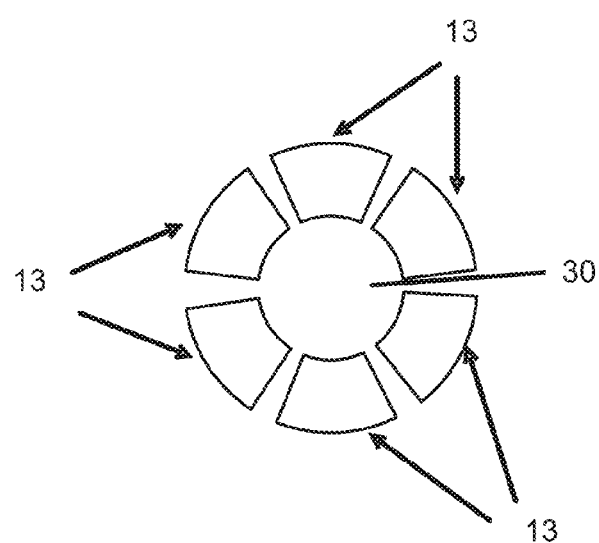

FIGS. 7 to 9 illustrate schematically different possible configurations of lumens in cut views.

More specifically, FIG. 7 shows a configuration with two lumens 11, FIG. 8 a configuration with three lumens 12 and FIG. 9 a configuration with six lumens 13.

Figure 10:
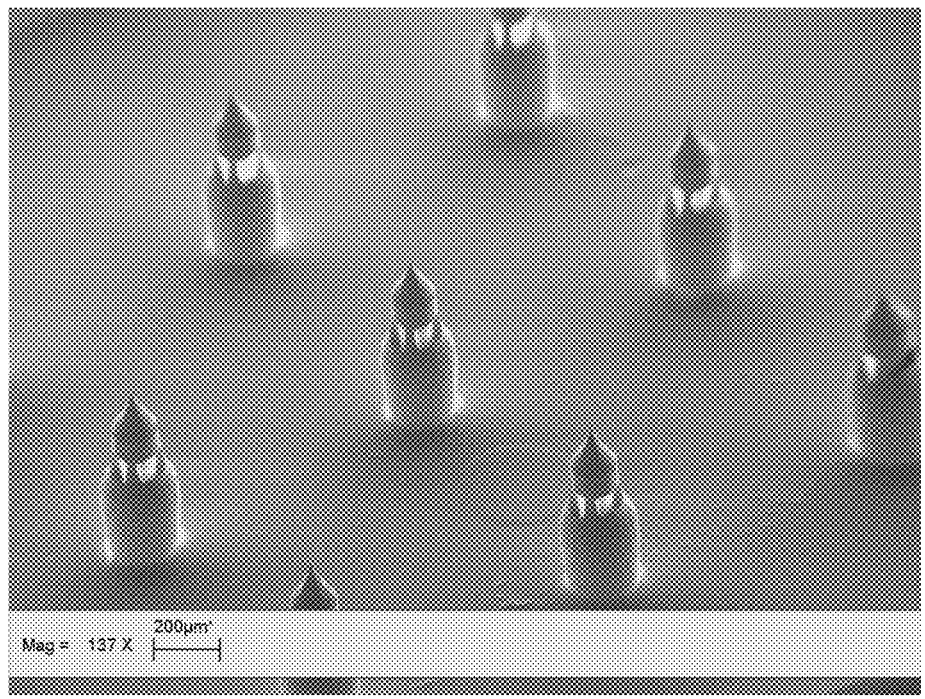
FIGS. 10 and 11 are SEM images of micro-needles according to the present invention.
Figure 11:
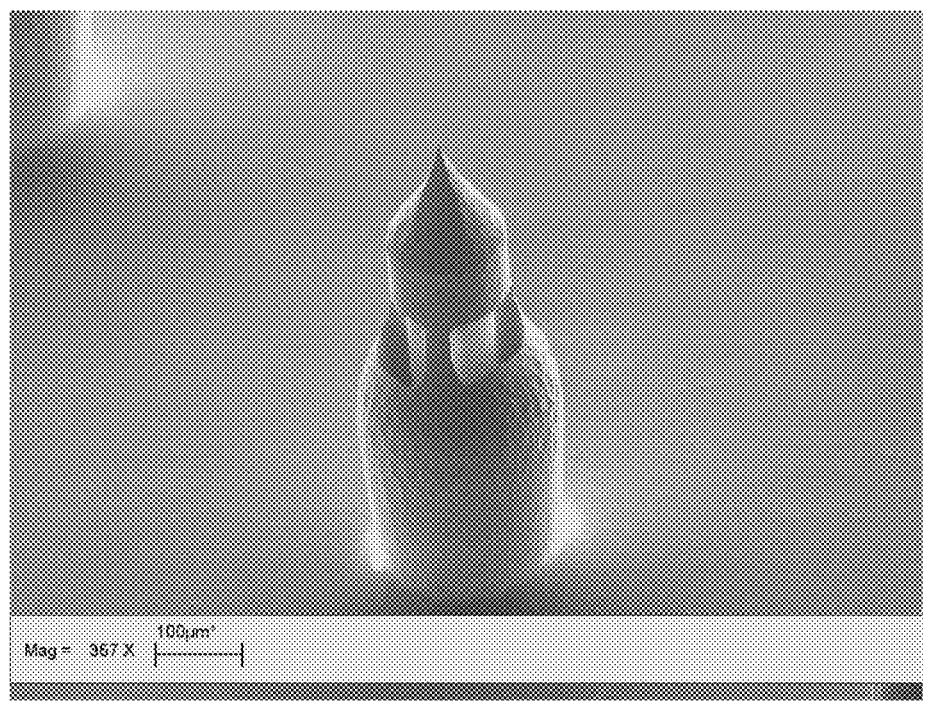

FIGS. 10 and 11 are SEM (scanning electron microscope) images of an array of micro-needles (FIG. 10) or a single micro-needle (FIG. 11) according to the present invention. This is an example where each micro-needle has three lumens.

Figure 12:
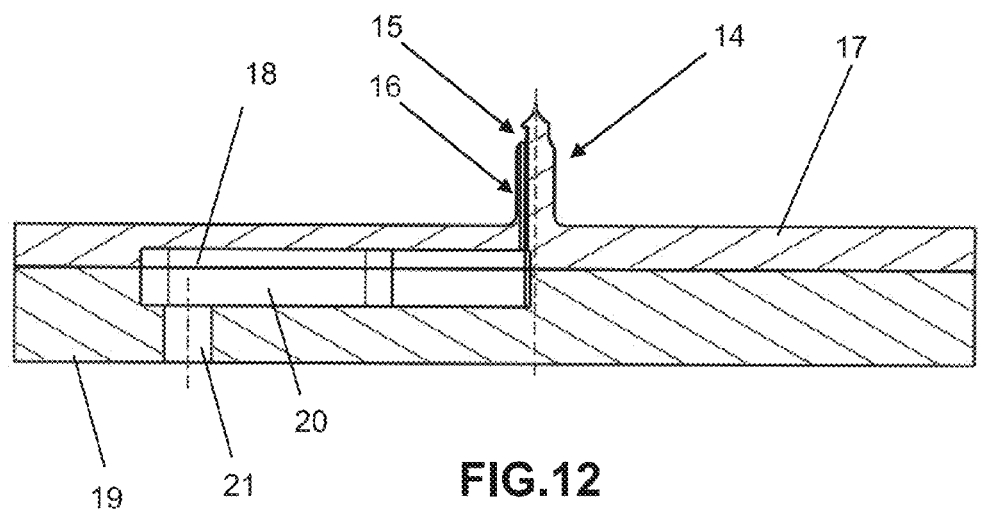
FIGS. 12 and 13 illustrate possible embodiments of reservoirs for the microneedles.
Figure 13:
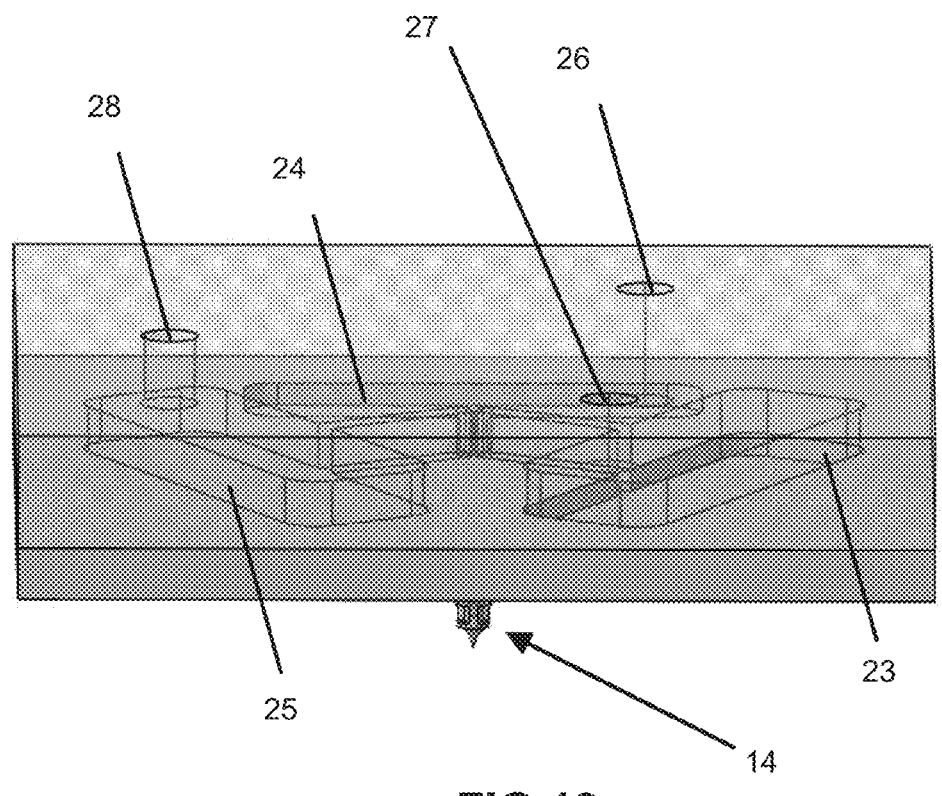

In FIGS. 12 and 13, one has illustrated possible embodiments of reservoirs for the microneedles. In the prior art, such reservoirs were typically made in a separate and/or independent part and then connected to the microneedles.

In the present invention, it is proposed to form the reservoirs directly in or partially in the support of the microneedles as illustrated in FIGS. 12 and 13. More specifically, in FIG. 12 one sees in a partial cut view a microneedle 14 with openings 15 in connection with lumens 16. The design of this needle is similar to the other needles illustrated in the previous figures. This needle 14 is formed with a base 17 (as the previous embodiments disclosed above) and said base 17 comprises a recess 18 forming a part of a reservoir. There is a further element 19 attached to the base 17. This element is made from an appropriate material, for example pyrex or any other suitable material and is attached to the base 17 for example by bonding. This element 19 also comprises a recess 20 and both recesses 18 and 20 form together the reservoir that is connected to the lumen 16. FIG. 12 also illustrates an inlet 21 for the reservoir for filling said reservoir with a drug or any other product to be used.

FIG. 13 illustrates a perspective view in transparency of an embodiment of a needle 22 with three reservoirs 23, 24 and 25, which is for example based on the example of FIG. 12. Also illustrated are three inlets 26, 27 and 28 for the reservoirs 23-25. Preferably, in this embodiment, each reservoir is connected to one lumen allowing this design to deliver up to three different products, i.e. drugs according to the principle of the present invention.

Of course, this is only an exemplary embodiment and variations are possible in the frame of the present invention.

Although the lumens are illustrated in the figures as being symmetrical in cross section, they of course can be asymmetrical and can have independent variable diameters representing different flow resistances. An example would be in the case of use of the micro-needle with a multiple drug delivery system, where different rates are required for each drug and similar pressure or diffusion characteristics are applicable to each the several drugs connected to a different channel. They also may have different shapes than that represented and different sizes and the number of lumens per needle is also not limited to the configurations illustrated here, i.e. at least two or more. Also, they may be distributed in a symmetrical or non symmetrical way around the longitudinal axis of the micro-needle. An example would be, in the case of interstitial fluid sampling and drug injection in diabetes patients, that the channels would be placed in opposite directions to limit cross interaction between insulin delivery and interstitial fluid sampling.

The shapes of the lumen in cross section can be a circle, a triangle, a polygon or any other suitable shape. The side-openings are always perpendicular to the lumen's axis.

As one will readily understand, the prior art designs with one single lumen only allowed the creation of one single injection site. With the present invention, it is possible to create a plurality of independent injection sites (one for each lumen). As said previously, this gives the possibility to inject different products, i.e. drugs (one per lumen), but also to inject a product in one lumen and to recuperate another product through another lumen (for example by aspiration), while limiting the interactions between the two fluids.

When using all the lumens for the same product (for example a drug), it is possible to obtain a better homogeneity around the micro-needle than what was previously possible with a single lumen. Also, by using more than one lumen for the same product, the overall fluidic resistance is reduced and a greater quantity of product can be injected during the same time duration thus improving the flow of the micro-needle while increasing the overall micro-needle resistance to breakage.

In one embodiment each lumen can be connected to a different reservoir when all the lumens are used to delivery a fluid or other equivalent product.

The lumens dimensions and design may be calculated in order to have different flow resistance, resulting in different flow rates.

In an embodiment, the micro-needle according of the present invention is used for the delivery of at least two drugs from a patch reservoir.

In an embodiment, the micro-needle is used for the delivery of at least one drug inside the skin (for example insulin) and a sampling of at least one substance from the skin (for example glucose from the interstitial fluid).

A preferred embodiment according to the present invention resides in the presence of a cylinder in the needle. This cylinder is visible and referenced as 30 in the FIGS. 3, and 7-9. As one can understand this cylinder typically present in the central area of the needle 4 (for example it extends axially) and is surrounded by the lumens/channels. The advantage of this cylinder (which is absent in the prior art), is that it reinforces the needle without changing the dimension of the needle and increases it resistance to breakage.

It is clear that all the embodiments described in the present application are non-limiting exemplary examples and other variants are possible in the scope of the present invention.

The invention claimed is:

1. A micro-needle comprising, along a longitudinal direction,
    an elongated body,
    a head,
    a structure, and
    a conical part,
    wherein the micro-needle further comprises
    at least two parallel independent lumens located along the longitudinal direction inside the elongated body and the head, each of the lumens communicating with a respective distal side opening of the head, at least one of said openings being essentially oriented in a direction which is perpendicular with respect to a corresponding lumen main direction,
    wherein a top end of each of the lumens is located in the head, and the conical part is located at a distal end of the micro-needle and includes a closed pointed end tip forming a tip of the micro-needle and an opposite end integrally formed with the head,
    wherein the structure is a solid cylinder arranged in a central area of the micro-needle.

2. The micro-needle according to claim 1 wherein each of said lumens is connected to a different reservoir.

3. The micro-needle according to claim 1 wherein the closed pointed end tip has a diameter of less than 1 μm.

4. The micro-needle according to claim 1 wherein the elongated body and the head have an external circular cross-section.

5. The micro-needle according to claim 1 wherein the elongated body and the head have an external polygonal cross-section.

6. The micro-needle according to claim 1 wherein the conical part of the micro-needle has a smaller external cross-section than an external cross-section of the elongated body.

7. The micro-needle according to claim 1, further comprising a base.

8. A group of said micro-needles according to claim 1, wherein the group of microneedles is fixed on a base.

9. The micro-needle as defined in claim 1 and obtained by a process comprising three isotropic etchings and two anisotropic etchings.

10. The micro-needle according to claim 1, wherein the solid cylinder is surrounded by said lumens.

11. The micro-needle according to claim 1, wherein the solid cylinder further comprises walls forming interior walls of said lumens.

12. A micro-needle comprising, along a longitudinal direction,
- an elongated body,
- a head,
- a cylindrical solid structure arranged inside the elongated body, and
- a conical part,
- wherein the micro-needle further comprises at least two parallel independent lumens located along the longitudinal direction and inside the elongated body and the head,
- each of the lumens communicating with a respective distal side opening of the head,
- at least one of the openings being essentially oriented in a direction which is perpendicular with respect to a corresponding lumen main direction,
- wherein a top end of each of the lumens is located in the head, and the conical part is located at a distal end of the micro-needle and includes a closed pointed end tip forming a tip of the micro-needle and an opposite end of the conical part is integrally formed with the head.

13. The micro-needle according to claim 12, wherein the cylindrical solid structure further comprises walls forming interior walls of said lumens.

14. The micro-needle according to claim 12, wherein the cylindrical solid structure is surrounded by said lumens.

* * * * *